(12) United States Patent
Chen et al.

(10) Patent No.: US 11,235,166 B2
(45) Date of Patent: Feb. 1, 2022

(54) TRANSCRANIAL MAGNETIC STIMULATION TREATMENT APPARATUS

(71) Applicants: SHENZHEN HANIX UNITED, LTD., Guangdong (CN); SHENZHEN MILEBOT ROBOTICS CO., LTD., Guangdong (CN)

(72) Inventors: Gong Chen, Guangdong (CN); Jing Ye, Guangdong (CN); Feng Xu, Guangdong (CN); Jialin Feng, Guangdong (CN); Guang Hu, Guangdong (CN)

(73) Assignees: SHENZHEN HANIX UNITED, LTD., Shenzhen (CN); SHENZHEN MILEBOT ROBOTICS CO., LTD., Shenzhen (CN)

( * ) Notice: Subject to any disclaimer, the term of this patent is extended or adjusted under 35 U.S.C. 154(b) by 291 days.

(21) Appl. No.: 16/469,653

(22) PCT Filed: Mar. 12, 2018

(86) PCT No.: PCT/CN2018/078706
§ 371 (c)(1),
(2) Date: Jun. 14, 2019

(87) PCT Pub. No.: WO2018/233323
PCT Pub. Date: Dec. 27, 2018

(65) Prior Publication Data
US 2020/0078599 A1    Mar. 12, 2020

(30) Foreign Application Priority Data
Jun. 20, 2017 (CN) .......................... 201710467812.0

(51) Int. Cl.
*A61N 2/00* (2006.01)
*A61N 2/02* (2006.01)
(Continued)

(52) U.S. Cl.
CPC .............. *A61N 2/006* (2013.01); *A61B 34/20* (2016.02); *A61B 34/30* (2016.02); *A61N 2/02* (2013.01); *A61B 2034/2055* (2016.02)

(58) Field of Classification Search
CPC .......... A61N 2/02; A61N 2/006; A61B 34/20; A61B 2034/2055; A61B 34/30;
(Continued)

(56) References Cited

FOREIGN PATENT DOCUMENTS

| CN | 106110507 A | * 11/2016 |
|----|-------------|-----------|
| CN | 106110507 A | 11/2016 |

OTHER PUBLICATIONS

English Translation of CN106110507A (Year: 2016).*

* cited by examiner

*Primary Examiner* — Christine H Matthews
*Assistant Examiner* — Joshua Daryl D Lannu (57) ABSTRACT

Disclosed is a transcranial magnetic stimulation treatment apparatus applicable to the technical field of medical devices, comprising a TMS coil, a support, a mechanical arm, a controller, and a positioning device. The positioning device detects the position of a human head and the TMS coil and sends positional information to the controller; the controller controls six driving mechanisms of the mechanical arm to rotate to a corresponding angle. Because the mechanical arm has six degrees of freedom, the TMS coil is capable of stimulating each cerebral region of the brain, and the positioning device is capable of detecting an accurate position of the human head, thereby controlling the mechanical arm to accurately position the TMS coil on the human head, and to reduce manual operation.

9 Claims, 7 Drawing Sheets

(51) Int. Cl.
*A61B 34/30* (2016.01)
*A61B 34/20* (2016.01)
(58) Field of Classification Search
CPC ...... B25J 9/1045; B25J 9/0018; B25J 19/068; B25J 9/102; B25J 9/046
See application file for complete search history.

TRANSCRANIAL MAGNETIC STIMULATION TREATMENT APPARATUS

TECHNICAL FIELD

The disclosure relates to the technical field of medical apparatus, and in particular to a Transcranial Magnetic Stimulation (TMS) therapy apparatus.

BACKGROUND

Statistics from the Mental Health Center of the Chinese Center for Disease Control and Prevention shows that there are more than 100 million of psychiatric disorders at present in China. However, less than 50% of the public know about psychiatric diseases, and the consultation rate is even lower. At present, about 20% of these psychiatric disorders get timely treatment, and the remaining 80% fail to get timely treatment or even fail to get the most basic treatment. The number of severe psychiatric disorders is up to 16 million. According to the latest statistical data from the IMS Health, medicines taken by psychotic disorders cost more than USD 36 billion worldwide, which takes up 1% of the total medicine sale amount. However, domestically, the market of medicines for psychotic diseases is relatively small, and the medicines for psychotic diseases take up about 1.5% of the total sale amount of hospitals. There are more than 600 hospitals for psychotic diseases in China. However, compared with the increasing incidence rate of psychotic diseases, there is a big gap between the number of hospitals and the demands from the psychotic disorders. Thus far, many of the psychotic disorders fail to get professional, systematical and effective treatment.

The Transcranial Magnetic Stimulation (TMS) is a technique that generates a current in a local brain cortex through a pulsed magnetic field, to temporarily activate or suppress the cortex.

TMS on the motor cortex can generate muscle twitches or stop movement. Stimulation on the occipital cortex can generate optical illusions or blind spots. TMS can change the function of the brain during a period of time after the stimulation.

TMS can treat psychotic disorders such as schizophrenia (negative symptoms), melancholia, obsessive compulsive disorder, hypomania, Post-traumatic Stress Disorder (PTSD) and the like. However, during TMS therapy, it is difficult to maintain accurate positioning, because the most commonly used positioning method is manually adjusting a position of the TMS coil with the aid of a visual navigation system. But since a single therapy process usually takes more than 30 minutes and the TMS coil usually has a weight of more than 2 kg. Thus, it is not practical to use the above positioning method. If the TMS coil is placed on a fixed support, it is not possible for the system to track a desired trace or compensate for a movement of the human head.

SUMMARY

The disclosure is intended to provide a TMS therapy apparatus, which aims to solve the problem in the prior art regarding difficulty in accurate positioning and impossibility of tracking a desired trace and compensating for movement of the human head.

The embodiments of the disclosure are implemented as follows. There is provided a Transcranial Magnetic Stimulation (TMS) therapy apparatus, including:

a TMS coil;

a support;

a robotic arm including a connection located at a bottom end of the robotic arm, a first drive mechanism driving the connection to rotate around a z-axis, a second drive mechanism driving the first drive mechanism to rotate around an x-axis, a third drive mechanism driving the second drive mechanism to rotate around the z-axis, a fourth drive mechanism driving the third drive mechanism to rotate around the x-axis, a fifth drive mechanism driving the fourth drive mechanism to rotate around the x-axis and a sixth drive mechanism driving the fifth drive mechanism to rotate around the z-axis, the sixth drive mechanism being secured to the support and the TMS coil being mounted on the connection;

a controller for controlling a rotation angle of each of the first drive mechanism, the second drive mechanism, the third drive mechanism, the fourth drive mechanism, the fifth drive mechanism and the sixth drive mechanism; and a positioning device for detecting a position of a human head and a position of the TMS coil, and for sending information about the positions to the controller, an output of the positioning device is electrically connected with an input of the controller, and an output of the controller is electrically connected with each of the drive mechanisms of the robotic arm.

In an embodiment, the positioning device includes a first infrared camera, a second infrared camera and a processor, herein the first infrared camera and the second infrared camera have capturing directions that are perpendicular to each other, and the first and second infrared cameras are located outboard of the TMS coil; the first and second infrared cameras send captured image information to the processor; and the processor processes the image information to obtain the position of the human head and the position of the TMS coil, and sends the information about the positions to the controller; and the controller controls the robotic arm to position the TMS coil at the human head.

In an embodiment, the fourth drive mechanism is a flexible driver including a fourth electric motor, a horizontal bevel gear, a vertical bevel gear, an output member, a first spring, a second spring, a pulley, a belt and an tightening device, herein the horizontal bevel gear is coaxially connected with an output shaft of the fourth electric motor, and the horizontal bevel gear and the vertical bevel gear are engaged with each other; the output member is connected fixedly with the vertical bevel gear; the pulley is connected coaxially and fixedly with the vertical bevel gear, and the belt is wound around the pulley and the tightening device; a first movable groove and a second movable groove that are symmetrical are provided on the vertical bevel gear, a first slot and a second slot that are symmetrical are arranged on a top of the output member, the first spring and the second spring are respectively held in the first slot and the second slot, and a stop is projected from each end of each of the first or second spring for restricting the range of motion of the first or second spring, respectively, herein stops on both ends of the first spring are configured to abut against groove walls on both ends of the first movable groove, and stops on both ends of the second spring are configured to abut against groove walls on both ends of the second movable groove.

In an embodiment, the sixth drive mechanism includes a sixth electric motor, a turntable and a sixth drive frame, the turntable being fixedly connected with an output shaft of the sixth electric motor, and a top portion of the sixth drive frame being fixedly connected with the turntable.

In an embodiment, the fifth drive mechanism includes a fifth electric motor arranged horizontally and a fifth drive frame, the fifth electric motor being mounted on the sixth drive frame, and the fifth drive frame being fixedly connected with an output shaft of the fifth electric motor.

In an embodiment, the fourth electric motor is secured on the fifth drive frame and the tightening device includes a tightening wheel and a stationary shaft, the stationary shaft being secured on the fifth drive frame, and the tightening wheel being rotatably fitted around the stationary shaft.

In an embodiment, the fourth drive mechanism further includes a fourth drive frame and a rotation shaft, the rotation shaft being fixedly connected with the vertical bevel gear, the rotation shaft passing rotatably through a bottom end of the fifth drive frame and being fixedly connected with a top end of the fourth drive frame, and the output member being also fixedly connected with the top end of the fourth drive frame.

In an embodiment, the third drive mechanism includes a third electric motor arranged vertically and a third drive frame, the third electric motor being secured on a bottom end of the fourth drive frame, and the third drive frame being fixedly connected with an output shaft of the third electric motor.

In an embodiment, the second drive mechanism includes a second electric motor arranged horizontally and a second drive frame that is below the third drive frame, herein the second drive frame has a second mount slot in which the second electric motor is fixedly mounted, an output shaft of the second electric motor passes through a slot wall of the second mount slot and is fixedly connected with the third drive frame, a second through hole is provided on the other slot wall of the second mount slot, a second stud is extended at a position of the third drive frame corresponding to the second through hole, and the second stud is extended into the second through hole.

In an embodiment, the first drive mechanism includes a first electric motor arranged vertically, the first electric motor being secured on a bottom end of the second drive frame, and an output shaft of the first electric motor being fixedly connected with the connection.

Compared with the prior art, the technical solution according to embodiments of the disclosure has the following beneficial effects. In the TMS therapy apparatus, the robotic arm has multiple degrees of freedom, and thus the TMS coil fixed on the robotic arm can stimulate any brain area of the whole brain. The positioning device of the TMS therapy apparatus can detect accurate positions of the TMS coil and the human head, thus the controller can control, according to position information, various drive mechanisms of the robotic arm to rotate so that the robotic arm can accurately position the TMS coil in a position of the human head. Thus, it is possible to reduce considerably operation steps performed manually and thus save the time for positioning. When the position of the human head changes, the positioning device can detect in real time a new position of the human head, and the controller can control, according to information about the new position, the robotic arm to position the TMS coil in the new position, thereby implement compensation for the movement of the human head. When the TMS coil is required to move according to a certain program, it is possible to load the program into the controller to enable the robotic arm to move according to a desired path. Thus, the therapy process is more standard and accurate, which facilitates recovery of patients.

BRIEF DESCRIPTION OF THE DRAWINGS

Exemplary description of one or more embodiments of the disclosure will be described with reference to the accompanying drawings, and the exemplary description is not to be construed as limiting the embodiments. In the accompanying drawings, like reference numerals refer to similar elements. These figures in the accompanying drawings are not drawn to scale and are intended to be merely illustrative and non-limiting, unless otherwise stated.

DETAILED DESCRIPTION

In order to make technical problems to be solved, technical solutions and advantages of the disclosure clearer, the disclosure will be further elaborated below in combination with the accompanying drawings and embodiments. It should be understood that the specific embodiments are only used to interpret the disclosure instead of limiting the disclosure.

Figure 1:
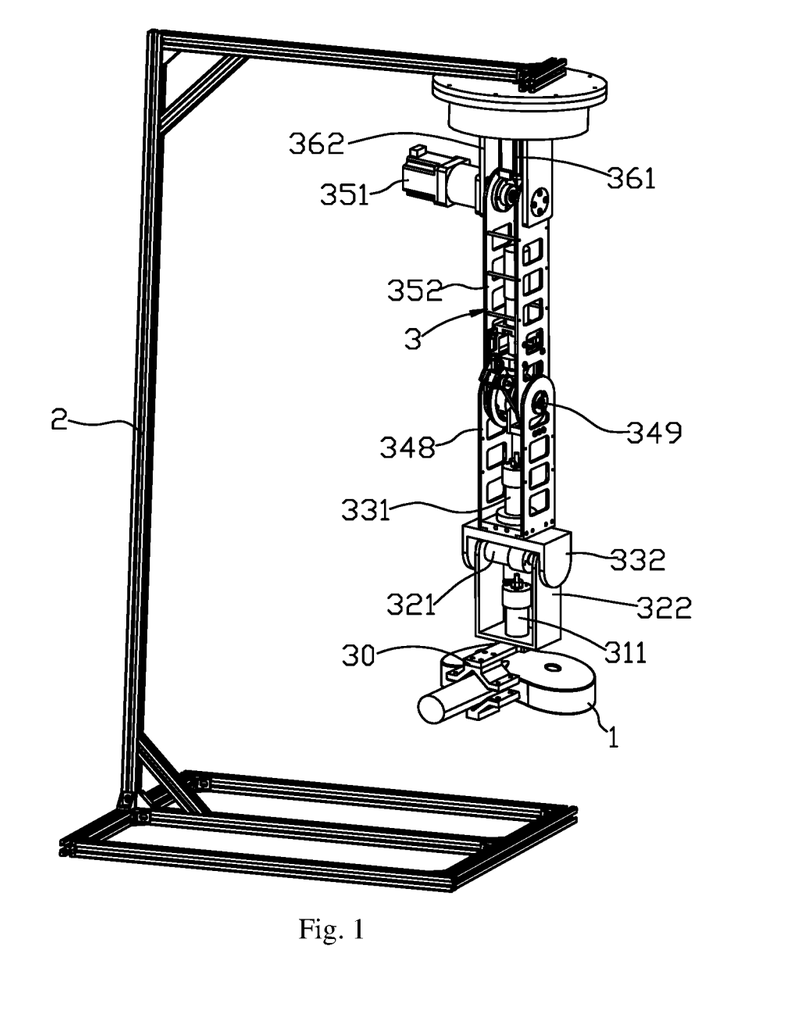
FIG. 1 is a schematic perspective view of a TMS therapy apparatus according to an embodiment of the disclosure.
Figure 2:
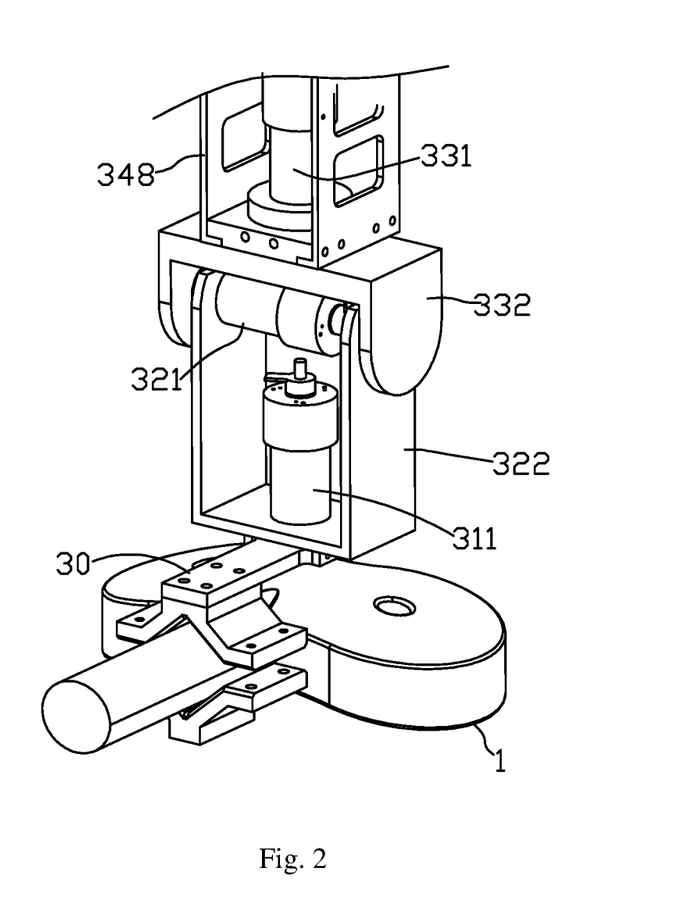
FIG. 2 is a schematic view of the TMS therapy apparatus as shown in FIG. 1, from another direction of view.
Figure 3:
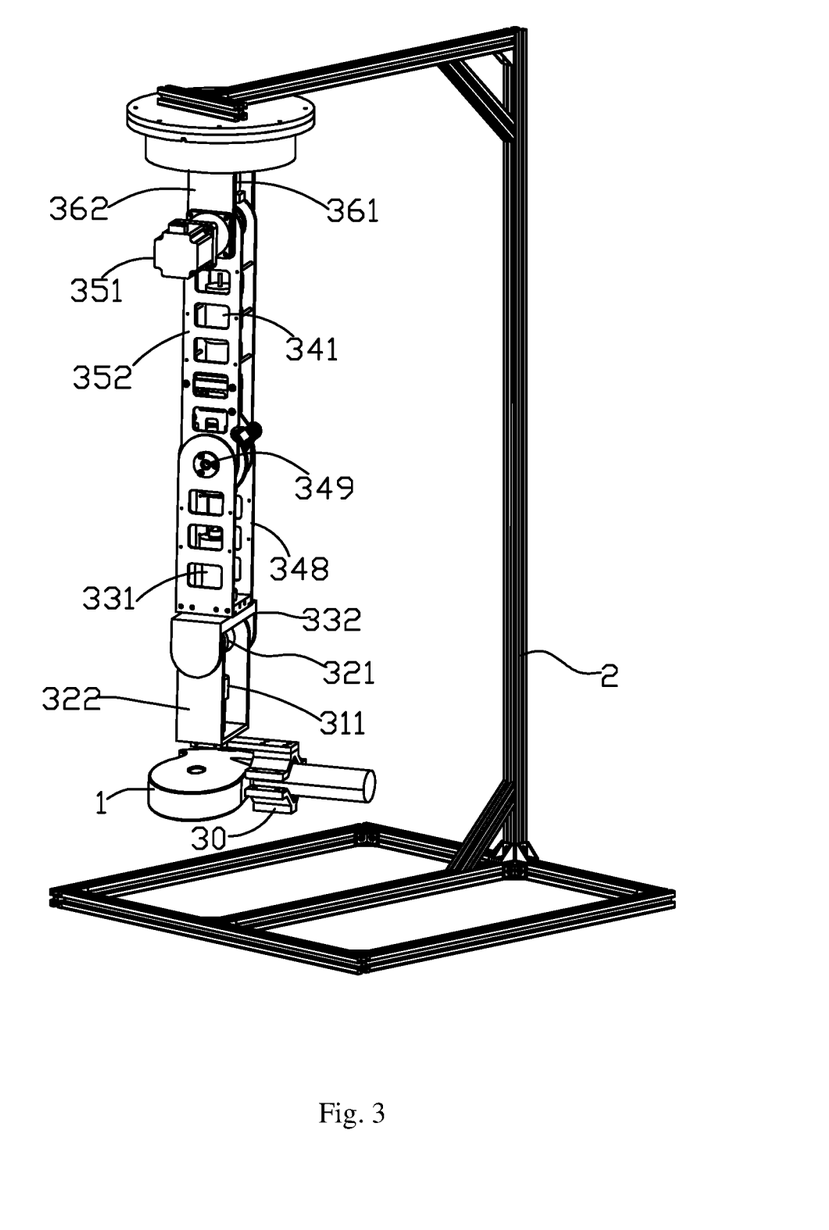
FIG. 3 is a partially enlarged schematic view of the TMS therapy apparatus as shown in FIG. 2.

FIGS. 1 to 3 show a preferred embodiment of the disclosure, which provides a Transcranial Magnetic Stimulation (TMS) therapy apparatus including a TMS coil 1, a support 2, a robotic arm 3, a controller 4 and a positioning device 5. The robotic arm 3 is mounted on the support 2, and the TMS coil 1 is mounted on the robotic arm 3; after detecting a position of a human head and a position of the TMS coil 1, the positioning device 5 is configured to send positional information to the controller 4; and the controller 4 is configured to control the robotic arm 3 to move.

Specifically, the robotic arm 3 includes a connection 30 located at a bottom end of the robotic arm 3, a first drive mechanism, a second drive mechanism, a third drive mechanism, a fourth drive mechanism, a fifth drive mechanism and a sixth drive mechanism. herein, the first drive mechanism is configured to drive the connection 30 to rotate around a z-axis, the second drive mechanism is configured to drive the first drive mechanism to rotate around an x-axis, the third drive mechanism is configured to drive the second drive mechanism to rotate around the z-axis, the fourth drive mechanism is configured to drive the third drive mechanism to rotate around the x-axis, the fifth drive mechanism is configured to drive the fourth drive mechanism to rotate around the x-axis, the sixth drive mechanism is configured to drive the fifth drive mechanism to rotate around the z-axis, the sixth drive mechanism is secured to the support 2 and the TMS coil 1 is mounted on the connection 30.

An output of the positioning device 5 is electrically connected with an input of the controller 4, and an output of the controller 4 is electrically connected with each of the drive mechanisms of the robotic arm 3.

Figure 4:
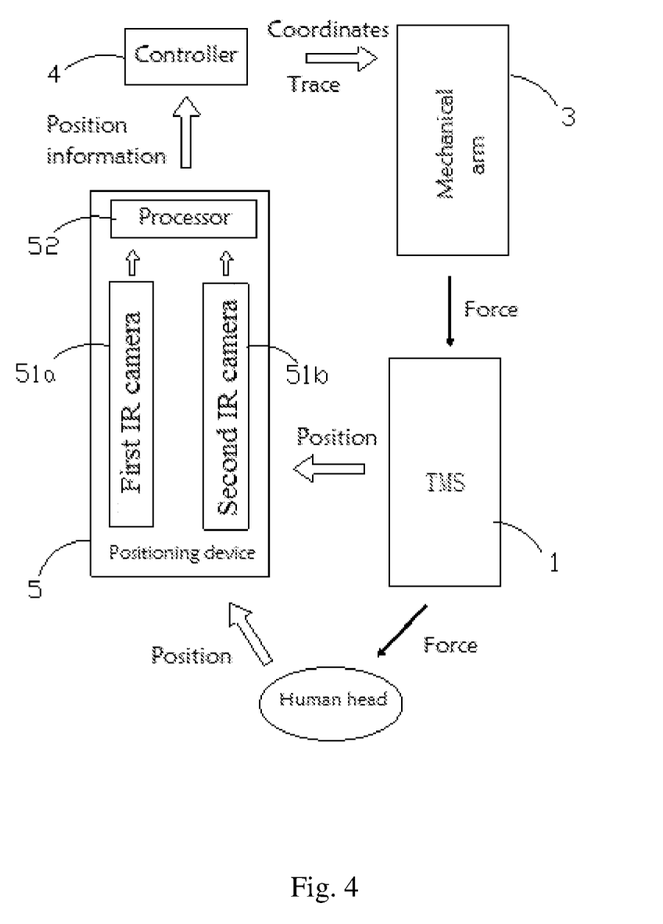
FIG. 4 is a block diagram of the TMS therapy apparatus as shown in FIG. 1.

Specifically, as shown in FIG. 4, the positioning device 5 includes a first infrared camera 51a, a second infrared camera 51b and a processor 52. The first infrared camera 51a and the second infrared camera 51b have capturing directions that are perpendicular to each other, and the first and second infrared cameras are located outboard of the TMS coil 1. Thus, the first infrared camera 51a and the second infrared camera 51b can each capture a two-dimensional image, and the combination of the two captured two-dimensional images can generate information about three-dimensional positions. The first and second infrared cameras 51a and 51b send captured image information to the processor 52; and the processor 52 processes the image information to obtain the position of the human head and the position of the TMS coil 1, and sends the information about the positions to the controller 4. The controller 4 is configured to control a rotation angle of each of the first drive mechanism, the second drive mechanism, the third drive mechanism, the fourth drive mechanism, the fifth drive mechanism and the sixth drive mechanism, so that the TMS coil 1 can move to the position of the human body.

As can be seen, in the TMS therapy apparatus, the robotic arm has six degrees of freedom, and thus the TMS coil fixed on the robotic arm 3 can stimulate any brain area of the whole brain. The positioning device 5 of the TMS therapy apparatus can detect accurate positions of the TMS coil 1 and the human head, thus the controller 4 can control, according to position information, various drive mechanisms of the robotic arm 3 to rotate so that the robotic arm 3 can accurately position the TMS coil 1 in a position of the human head. Thus, it is possible to reduce considerably the operation steps performed manually and thus save the time for positioning. When the position of the human head changes, the positioning device 5 can detect in real time a new position of the human head, and the controller 4 can control, according to information on the new position, the robotic arm 3 to position the TMS coil 1 in the new position, thereby compensate for the movement of the human head. When the TMS coil 1 is required to move according to a certain path, it is possible to load a program into the controller to enable the robotic arm 3 to move according to the desired path. Thus, the therapy process is made more standard and accurate, which facilitates recovery of patients.

The specific structures and operation processes of the robotic arm having six degrees of freedom according embodiments of the disclosure will be elaborated below.

The sixth drive mechanism includes a sixth electric motor 361, a turntable (not shown) and a sixth drive frame 362. The turntable is connected fixedly with an output shaft of the sixth electric motor 361, the top of the sixth drive frame 362 is fixedly connected with the turntable. When the sixth electric motor 361 operates, its output shaft drives the turntable to rotate a certain angle around z-axis, and the sixth drive frame 362 secured below the turntable will also rotate the same angle accordingly.

The fifth drive mechanism includes a fifth electric motor 351 arranged horizontally and a fifth drive frame 352, the fifth electric motor 351 being mounted on the sixth drive frame 362, and the fifth drive frame 352 being fixedly connected with an output shaft of the fifth electric motor 351. The sixth drive frame 362 can rotate, causing positions of the fifth electric motor 351 and the fifth drive frame 352 to change. When the fifth electric motor 351 rotates, it makes the fifth drive frame to rotate around x-axis.

Figure 5:
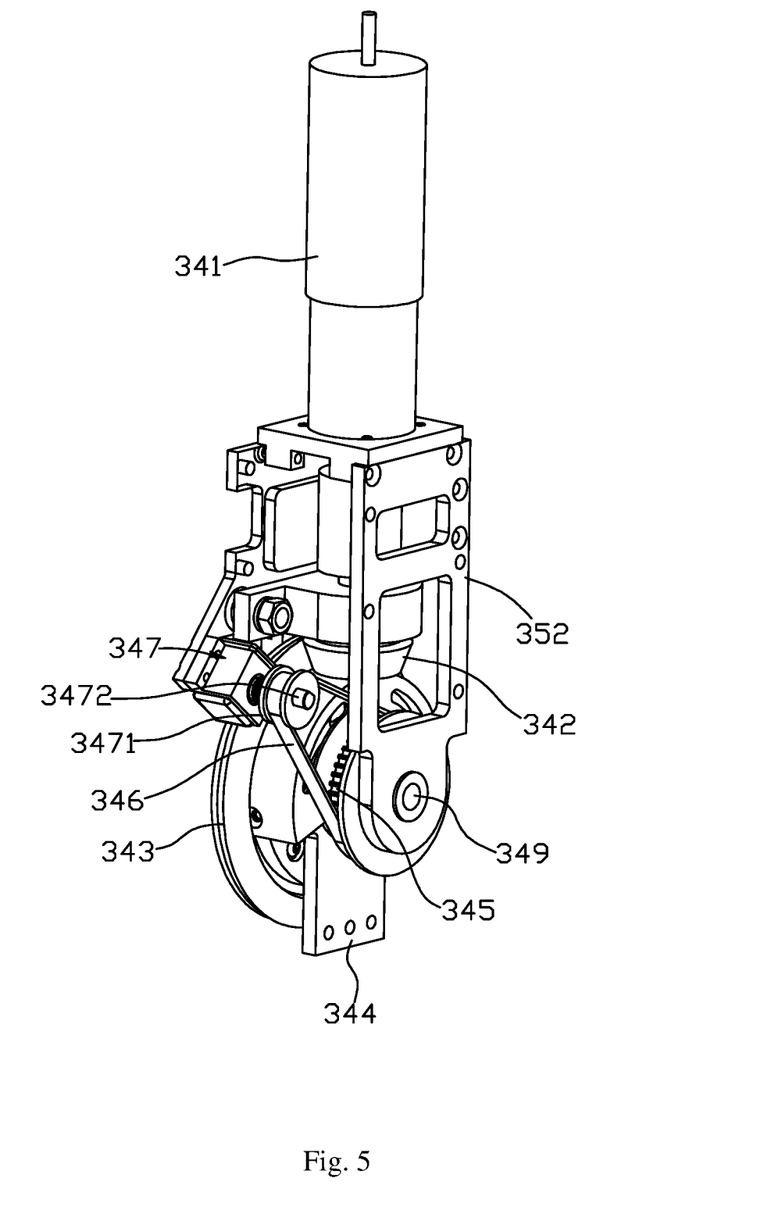
FIG. 5 is a schematic perspective structural view of a flexible driver of the TMS therapy apparatus as shown in FIG. 1.
Figure 6:
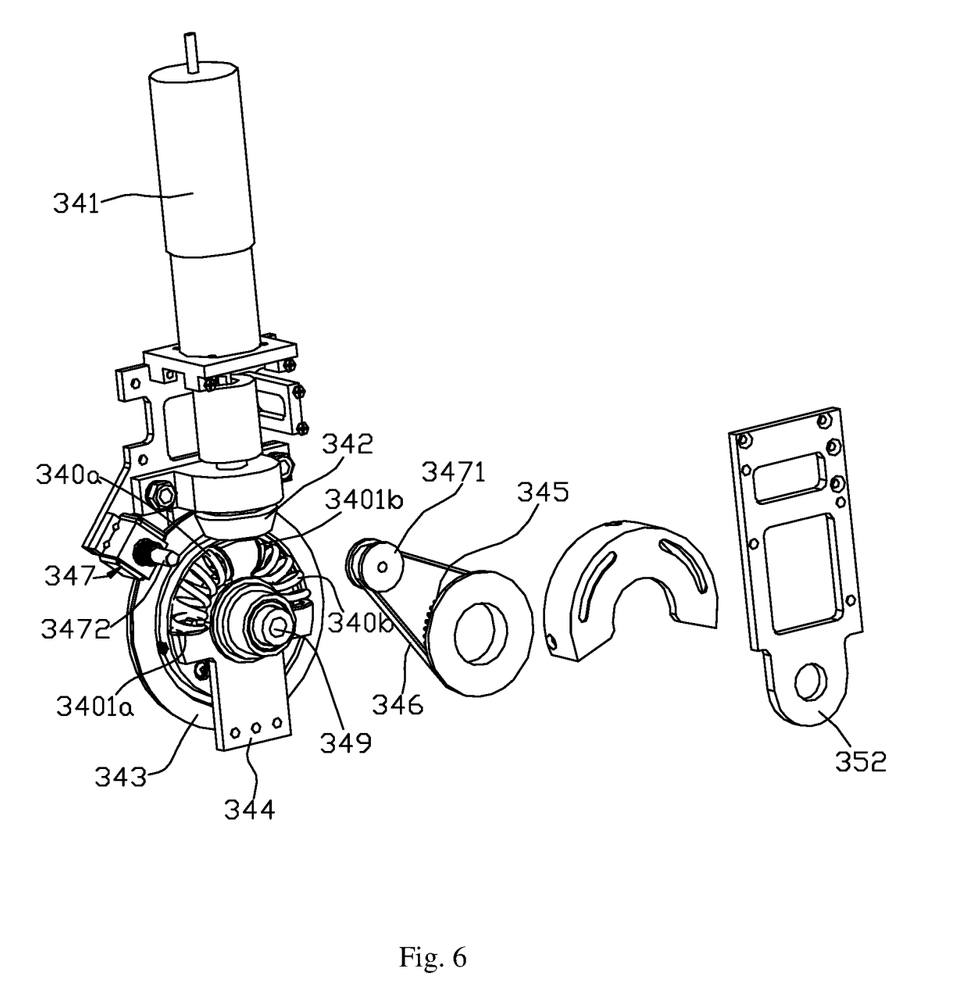
FIG. 6 is an exploded structural view of the flexible driver as shown in FIG. 5.

Referring to FIG. 5 and FIG. 6, the fourth drive mechanism is a flexible driver including a fourth electric motor 341, a horizontal bevel gear 342, a vertical bevel gear 342, an output member 344, a pulley 345, a belt 346, an tightening device 347, a fourth drive frame 348, a rotation shaft 349, a first spring 340a and a second spring 340b. The horizontal bevel gear 342 is coaxially connected with an output shaft of the fourth electric motor 341, and the horizontal bevel gear 342 and the vertical bevel gear 343 are engaged with each other; the output member 344 is connected fixedly with the vertical bevel gear 343. A first movable groove and a second movable groove that are symmetrical are provided on the vertical bevel gear 343, a first slot and a second slot that are symmetrical are arranged on a top of the output member 344, the first spring 340a and the second spring 340b are respectively held in the first slot and the second slot. A stop 3401a is projected from either end of the first spring 340a for restricting the range of motion of the first spring 340a, and a stop 3401b is projected from either end of the second spring 340b for restricting the range of motion of the second spring 340b; herein stops 3401a on both ends of the first spring 340a can abut against groove walls on both ends of the first movable groove, and stops 3401b on both ends of the second spring 340b can abut against groove walls on both ends of the second movable groove.

The pulley 345 is connected coaxially and fixedly with the vertical bevel gear 343, and the belt 346 is wound around the pulley 345 and the tightening device 347. The fourth electric motor 341 is secured on the fifth drive frame 352. The tightening device 347 includes an tightening wheel 3471 and a stationary shaft 3472, the stationary shaft 3472 being secured on the fifth drive frame, and the tightening wheel 3471 being rotatably fitted around the stationary shaft 3472. The rotation shaft 349 is fixedly connected with the vertical bevel gear 343, the rotation shaft 349 passes rotatably through a bottom end of the fifth drive frame 352 and fixedly connected with a top end of the fourth drive frame 348, and the output member 344 is also fixedly connected with the top end of the fourth drive frame 348.

When the fourth electric motor operates, the horizontal bevel gear 342 rotates around x-axis, and the horizontal bevel gear 342 directly drives the vertical bevel gear 343 engaged therewith to rotate around x-axis; when the vertical bevel gear 343 rotates, the output member 344 and rotation shaft 349 connected therewith drive and it drives the fourth drive frame 348 to rotate. When the vertical bevel gear 343 rotates, the pulley connected therewith is constrained by the belt 346, thus the fourth drive frame 348 achieves effect of elastic swing, which facilitates improvement in comfort level when the TMS coil 1 is placed on the human head.

Figure 7:
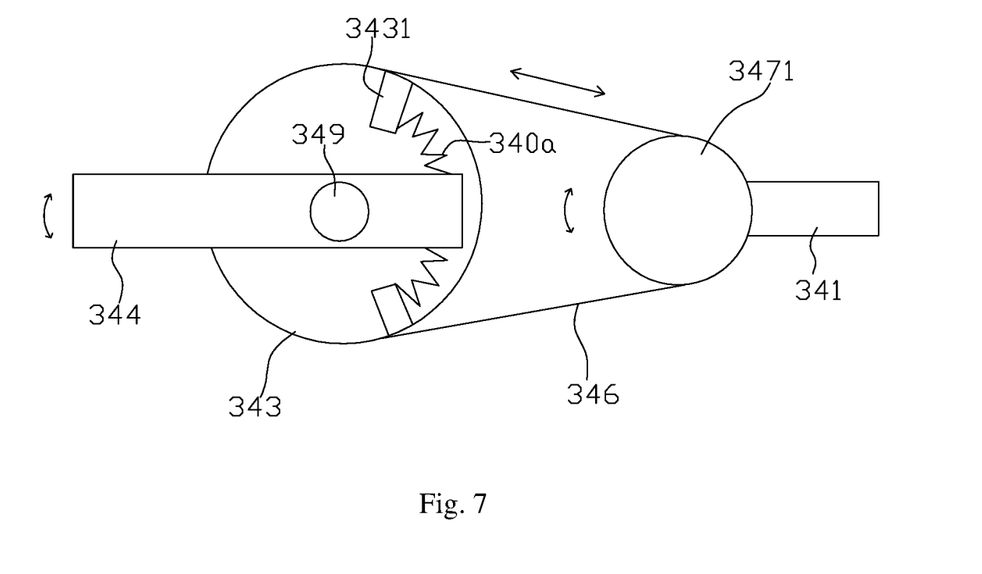
FIG. 7 is a schematic view that shows different forces as controlled by the flexible driver as shown in FIG. 5 are acted on the output member.

On the other hand, in addition to aiding positioning of the TMS coil 1 through swing, the flexible driver according to the embodiment of the disclosure can also control or adjust the TMS coil 1 so that different forces can be applied to the human head by the TMS coil 1. As shown in FIG. 7, the swing angle and direction of the vertical bevel gear 343 is controlled by the fourth electric motor 341. When the vertical bevel gear 343 swings in the clockwise direction, the groove wall 3431 on the end of the first movable groove abuts against the first spring 340a, the first spring 340a is compressed under the force, and the elastic force of the first spring 340a under the compressed state is applied on the head after passing by the output member 344 and the TMS coil 1. Thus, by controlling the angle of clockwise rotation of the fourth electric motor 341, it is possible to control the amount of compression of the first spring 340a. Since different amounts of compression of the first spring 340a can generate different presses on the output member 344 (the more the amount of compression, the bigger the press), the TMS coil 1 can be controlled through the flexible driver according to the embodiment of the disclosure so that different forces are applied on one side of the head. Similarly, controlling the fourth electric motor to counterclockwise rotate different angles, will control the TMS coil 1 to apply different forces on the other side of the head.

The third drive mechanism includes a third electric motor 331 and a third drive frame 332 which are arranged vertically, the third electric motor 331 being secured on a bottom end of the fourth drive frame 348, and the third drive frame 332 being fixedly connected with an output shaft of the third electric motor 331. When the electric motor 331 operates, it drives the third drive frame 332 to rotate around z-axis.

The second drive mechanism includes a second electric motor 321 arranged horizontally and a second drive frame 322 that is below the third drive frame 332, herein the second drive frame 322 has a second mount slot 3231 in which the second electric motor 321 is fixedly mounted, and an output shaft of the second electric motor 321 passes through a slot wall of the second mount slot 3231 and is fixedly connected with the third drive frame 332; the rotation of the third drive frame 332 will cause the positions of the second electric motor 321 and the second drive frame 322 to change. When the second electric motor operates, the second drive frame 322 rotates around x-axis. A second through hole 3232 is provided on the other slot wall of the second mount slot 3231, a second stud 3321 is extended at a position of the third drive frame 332 corresponding to the second through hole 3232, and the second stud 3321 is extended into the second through hole 3232, thus the second stud 3321 plays a part in supporting the second electric motor 321, the second mount 323 and the second drive frame 322 below the second stud 3321.

The first drive mechanism includes a first electric motor 311 arranged vertically, the first electric motor 311 being secured at a bottom end of the second drive frame 322, and an output shaft of the first electric motor 311 being fixedly connected with the connection 30. When the first electric motor operates, it drives the connection 30 to rotate. The TMS coil is installed to the connection 30, thus through driving of the various drive mechanism, the TMS coil 1 is caused to move firstly to a position of the human head in the three-dimensional space, and then apply a press on an accurately local portion.

What described hereinabove are merely preferable embodiments of the disclosure, and are not intended to limit the disclosure. All modifications, replacements and improvements made within the spirit and principles of the disclosure should be included within the scope of the disclosure.

The invention claimed is:

1. A Transcranial Magnetic Stimulation (TMS) therapy apparatus, comprising a TMS coil, wherein the TMS therapy apparatus further comprises:
   a support;
   a robotic arm comprising a connection located at a bottom end of the robotic arm, a first drive mechanism driving the connection to rotate around a z-axis, a second drive mechanism driving the first drive mechanism to rotate around an x-axis, a third drive mechanism driving the second drive mechanism to rotate around the z-axis, a fourth drive mechanism driving the third drive mechanism to rotate around the x-axis, a fifth drive mechanism driving the fourth drive mechanism to rotate around the x-axis and a sixth drive mechanism driving the fifth drive mechanism to rotate around the z-axis, the sixth drive mechanism being secured to the support and the TMS coil being mounted to the connection;
   a controller configured for controlling a rotation angle of each of the first drive mechanism, the second drive mechanism, the third drive mechanism, the fourth drive mechanism, the fifth drive mechanism and the sixth drive mechanism; and
   a positioning device arranged for detecting a position of a human head and a position of the TMS coil, and for sending positional information to the controller,
   wherein an output of the positioning device is electrically connected with an input of the controller, and an output of the controller is electrically connected with each of the drive mechanisms of the robotic arm, wherein
   the positioning device comprises a first infrared camera, a second infrared camera and a processor, wherein the first infrared camera and the second infrared camera have capturing directions that are perpendicular to each other, and the first and second infrared cameras are located outboard of the TMS coil; the first and second infrared cameras send captured image information to the processor; and the processor processes the image information to obtain the position of the human head and the position of the TMS coil, and sends the positional information to the controller; and the controller is configured to control the robotic arm to position the TMS coil at the human head.

2. The TMS therapy apparatus according to claim 1, wherein the fourth drive mechanism is a flexible driver comprising an electric motor, a horizontal bevel gear, a vertical bevel gear, an output member, a first spring, a second spring, a pulley, a belt and a tightening device, wherein the horizontal bevel gear is coaxially connected with an output shaft of the fourth electric motor, and the horizontal bevel gear and the vertical bevel gear are engaged with each other; the output member is connected fixedly with the vertical bevel gear; the pulley is connected coaxially and fixedly with the vertical bevel gear, and the belt is wound around the pulley and the tightening device; a first movable groove and a second movable groove that are symmetrical are provided on the vertical bevel gear, a first slot and a second slot that are symmetrical are arranged on a top of the output member, the first spring and the second spring are respectively held in the first slot and the second slot, and a stop is projected from each end of each of the first and second spring for restricting the range of motion of the first and second spring, wherein stops on both ends of the first spring are configured to abut against groove walls on both ends of the first movable groove, and stops on both ends of the second spring are configured to abut against groove walls on both ends of the second movable groove.

3. The TMS therapy apparatus according to claim 2, wherein the sixth drive mechanism comprises an electric motor, a turntable and a drive frame, the turntable being fixedly connected with an output shaft of the sixth drive mechanism's electric motor, and a top portion of the sixth drive mechanism's drive frame being fixedly connected with the turntable.

4. The TMS therapy apparatus according to claim 3, wherein the fifth drive mechanism comprises an electric motor arranged horizontally and a drive frame, the fifth drive mechanism's electric motor being mounted on the sixth drive mechanism's drive frame, and the fifth drive mechanism's drive frame being fixedly connected with an output shaft of the fifth drive mechanism's electric motor.

5. The TMS therapy apparatus according to claim 4 wherein the fourth drive mechanism's electric motor is secured on the fifth drive mechanism's drive frame and the tightening device comprises a tightening wheel and a stationary shaft, the stationary shaft being secured on the fifth drive mechanism's drive frame, and the tightening wheel being rotatably fitted around the stationary shaft.

6. The TMS therapy apparatus according to claim 5, wherein the fourth drive mechanism further comprises a drive frame and a rotation shaft, the rotation shaft being fixedly connected with the vertical bevel gear, the rotation shaft passing rotatably through a bottom end of the fifth drive mechanism's drive frame and being fixedly connected with a top end of the fourth drive mechanism's drive frame, and the output member being also fixedly connected with the top end of the fourth drive mechanism's drive frame.

7. The TMS therapy apparatus according to claim 6 wherein the third drive mechanism comprises an electric motor arranged vertically and a drive frame, the third drive mechanism's electric motor being secured on a bottom end of the fourth drive mechanism's drive frame, and the third drive mechanism's drive frame being fixedly connected with an output shaft of the third drive mechanism's electric motor.

8. The TMS therapy apparatus according to claim 7, wherein the second drive mechanism comprises an electric motor arranged horizontally and a drive frame that is below the third drive mechanism's drive frame, wherein the second drive mechanism's drive frame has a second mount slot in which the second drive mechanism's electric motor is fixedly mounted, an output shaft of the second drive mechanism's electric motor passes through a slot wall of the second mount slot and is fixedly connected with the third drive mechanism's drive frame, a second through hole is provided on another slot wall of the second mount slot, a second stud is extended at a position of the third drive mechanism's drive frame corresponding to the second through hole, and the second stud is extended into the second through hole.

9. The TMS therapy apparatus according to claim 8, wherein the first drive mechanism comprises a first electric motor arranged vertically, the first electric motor being secured on a bottom end of the second drive mechanism's drive frame, and an output shaft of the first electric motor being fixedly connected with the connection.

\* \* \* \* \*